US00PP14408P29

(12) United States Plant Patent
Chisholm

(10) Patent No.: US PP14,408 P2
(45) Date of Patent: Dec. 23, 2003

(54) GERANIUM PLANT NAMED 'FN CHOCOLATE'

(50) Latin Name: *Pelargonium X domesticum*
Varietal Denomination: FN Chocolate

(75) Inventor: David Ian Chisholm, Norwich (GB)

(73) Assignee: Floranova Ltd., Norfolk (GB)

( * ) Notice: Subject to any disclaimer, the term of this patent is extended or adjusted under 35 U.S.C. 154(b) by 0 days.

(21) Appl. No.: 10/176,717

(22) Filed: Jun. 21, 2002

(51) Int. Cl.[7] ..... A01H 5/00
(52) U.S. Cl. ..... Plt./331
(58) Field of Search ..... Plt./331

*Primary Examiner*—Kent Bell
*Assistant Examiner*—Louanne Krawczewicz Myers
(74) *Attorney, Agent, or Firm*—C. A. Whealy

(57) ABSTRACT

A new and distinct cultivar of Geranium plant named 'FN Chocolate', characterized by its upright, outwardly spreading and mounded growth habit; freely branching habit; dense and full plant habit; freely flowering habit; dark purple-colored flowers; and no requirement for vernalization.

1 Drawing Sheet

Botanical classification/cultivar designation: *Pelargonium×domesticum* cultivar FN Chocolate.

BACKGROUND OF THE INVENTION

The present invention relates to a new and distinct cultivar of Geranium plant, commercially known as Regal Geranium, botanically known as *Pelargonium×domesticum,* and hereinafter referred to by the name 'FN Chocolate'.

The new Regal Geranium is a product of a planned breeding program conducted by the Inventor in Foxley, Norfolk, United Kingdom. The objective of the breeding program is to develop new Regal Geranium cultivars with compact growth habit, numerous flowers, and interesting flower and foliage colors that do not require vernalization for flowering.

The new Regal Geranium originated from a self-pollination made by the Inventor in May, 1997 of a proprietary *Pelargonium×domesticum* selection identified as RPOAU, not patented. The cultivar FN Chocolate was discovered and selected by the Inventor as a flowering plant within the progeny from this self-pollination in a controlled environment in Foxley, Norfolk, United Kingdom.

Asexual reproduction of the new cultivar by terminal cuttings taken at Foxley, Norfolk, United Kingdom, since January, 1998 has shown that the unique features of this new Regal Geranium are stable and reproduced true to type in successive generations of asexual reproduction.

SUMMARY OF THE INVENTION

The following traits have been repeatedly observed and are determined to be the unique characteristics of 'FN Chocolate'. These characteristics in combination distinguish 'FN Chocolate' as a new and distinct Regal Geranium cultivar:

1. Upright, outwardly spreading and mounded growth habit.
2. Freely branching habit; dense and full plant habit.
3. Freely flowering habit.
4. Dark purple-colored flowers.
5. No requirement for vernalization.

Plants of the new Regal Geranium differ primarily from plants of the parent selection in the following characteristics:

1. Plants of the new Regal Geranium are more compact than plants of the selection RPOAU.
2. Plants of the new Regal Geranium flower earlier than plants of the selection RPOAU.

The new Regal Geranium can be compared to the cultivar, Burghi, not patented. However, in side-by-side comparisons conducted in Foxley, Norfolk, United Kingdom, plants of the new Regal Geranium differed from plants of the cultivar Burghi in the following characteristics:

1. Plants of the new Regal Geranium were more freely branching than plants of the cultivar Burghi.
2. Plants of the new Regal Geranium had smaller flowers than plants of the cultivar Burghi.
3. Plants of the new Regal Geranium and the cultivar Burghi differed in flower coloration.
4. Plants of the new Regal Geranium did not require vernalization for flowering whereas plants of the cultivar Burghi required vernalization for flowering.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Flower and foliage colors in the photographs may differ slightly from the color values cited in the detailed botanical description which accurately describe the colors of the new Regal Geranium.

The photograph at the top of the sheet comprises a side perspective view of a typical flowering plant of 'FN Chocolate'.

The photograph at the bottom of the sheet comprises a close-up view of a typical open flower, a typical flowering umbel, a typical flower bud, the lower surface of a typical developing leaf, and the upper surface of a typical mature leaf.

DETAILED BOTANICAL DESCRIPTION

The cultivar FN Chocolate has not been observed under all possible environmental conditions. The phenotype may vary somewhat with variations in environment such as temperature and light intensity, without, however, any variance in genotype. The aforementioned photographs and following observations and measurements describe plants grown in Lompoc, Calif., under commercial practice in a polycarbonate-covered greenhouse during the winter and spring with day temperatures ranging from 55 to 75° F., night temperatures ranging from 50 to 65° F. and light levels ranging from 4,000 to 8,000 foot-candles. Plants used for the photographs and description were about 22 weeks from planting rooted cuttings and were grown in gallon containers. In the following description, color references are made to The Royal Horticultural Society Colour Chart, 1995 Edition, except where general terms of ordinary dictionary significance are used.

Botancial classification: *Pelargonium×domesticum* cultivar FN Chocolate.

Parentage: Self-pollination of a proprietary *Pelargonium× domesticum* selection identified as RPOAU, not patented.

Propagation:

*Type cutting.*—Terminal cuttings.

*Time to initiate roots.*—About 7 days at 70° F.

*Time to develop roots.*—About 21 days at 70° F.

*Root description.*—Fine, freely branching.

Plant description:

*General appearance.*—Upright and outwardly spreading; mounded growth habit. Appropriate for gallon containers.

*Growth and branching habit.*—Vigorous and freely branching with about 16 lateral branches per plant; dense and full plant habit. Pinching is typically not required.

*Plant height* (*to top of foliage*).—About 30 cm.

*Plant height* (*to top of flowering umbels*).—About 37 cm.

*Plant width.*—About 46 cm.

*Lateral branches.*—Length: About 22 cm. Diameter: About 7 mm. Internode length: About 2.2 cm. Texture: Pubescent. Color: 144B.

*Foliage description.*—

*Arrangement.*—Before flowering, alternate; after flowering, opposite, simple. Length: About 6 cm. Width: About 9 cm. Shape: Roughly hemispherical, three-lobed. Apex: Rounded acute. Base: Truncate. Margin: Serrate; undulate. Venation: Palmate. Texture, upper surface: Slightly pubescent. Texture, lower surface: Glabrous. Color: Young foliage, upper surface: 146A. Young foliage, lower surface: 146B. Mature foliage, upper surface: 146A. Mature foliage, lower surface: 147B. Venation, upper surface: 146B. Venation, lower surface: 147C. Petiole: Length: About 8 cm. Diameter: About 3 mm. Texture, upper and lower surfaces: Glabrous. Color, upper and lower surfaces: 146A.

Flower description:

*Flower arrangement and type.*—Single rounded flowers arranged in hemispherical umbels arising from apical leaf axils. Umbels displayed above and beyond the foliage. At full flowering, usually about 50 open and developing umbels per plant. Umbels persistent. Flowers not fragrant.

*Flowering season.*—Year-round under greenhouse conditions; vernalization is not required for flowering. In the garden, flowering is continuous from spring until fall. Plants start flowering about 20 weeks after planting.

*Flower longevity.*—Flowers last about 5 to 7 days on the plant.

*Umbels/flowers.*—Height: About 5.5 cm. Diameter: About 9 cm. Number of flowers per umbel: About five. Flower diameter: About 4.5 cm. Flower depth (height): About 3.5 cm.

*Flower buds.*—Length: About 2 cm. Diameter: About 5 mm. Shape: Elongated ovoid. Color: More purple than 202B.

*Petals.*—Quantity: About five per flower arranged in a single whorl. Length, upper two petals: About 3.5 cm. Length, lower three petals: About 3.4 cm. Width, upper two petals: About 2.5 cm. Width, lower three petals: About 2 cm. Shape: Obovate. Apex: Rounded. Base: Attenuate. Margin: Entire. Texture, upper and lower surfaces: Smooth; satiny. Color: When opening, upper surface: Darker than 79A. When opening, lower surface: 79A. Fully opened, upper and lower surfaces: Darker than 79A; towards base, 57D with development, fading to close to 57D towards apex and margins.

*Sepals.*—Quantity: Five per flower arranged in a single whorl. Length, upper and lower sepals: About 2 cm. Width, upper two sepals: About 7 mm. Width, lower three sepals: About 5 mm. Shape: Elliptic. Apex: Acuminate. Base: Attenuate. Margin: Entire. Texture, upper and lower surfaces: Glabrous. Color, upper surface: 146B. Color, lower surface: 146A.

*Peduncle* (*umbel stem*).—Length: About 4.5 cm. Diameter: About 2 mm. Angle: About 45° from lateral branch. Strength: Strong. Texture: Slightly pubescent. Color: 144B.

*Pedicel* (*individual flower stem*).—Length: About 1.8 cm. Diameter: About 1 mm. Angle: About 30° from vertical. Strength: Strong. Texture: Slightly pubescent. Color: 144B.

*Reproductive organs.*—Androecium: Anther quantity: Six per flower. Anther shape: Elongated oblong. Anther size: About 1 mm by 3 mm. Anther color: 59A. Pollen amount: Scarce. Pollen color: 33A. Gynoecium: Pistil quantity: One per flower. Pistil length: About 2 cm. Stigma shape: Five-parted, star-shaped. Stigma color: 59A. Style length: About 1.7 cm. Style color: 61C. Ovary color: 144B.

*Seed/fruit.*—None observed.

Disease/pest resistance: Resistance to pathogens and pests common to Regal Geraniums has not been observed.

It is claimed:

1. A new and distinct cultivar of Geranium plant named 'FN Chocolate', as herein illustrated and described.

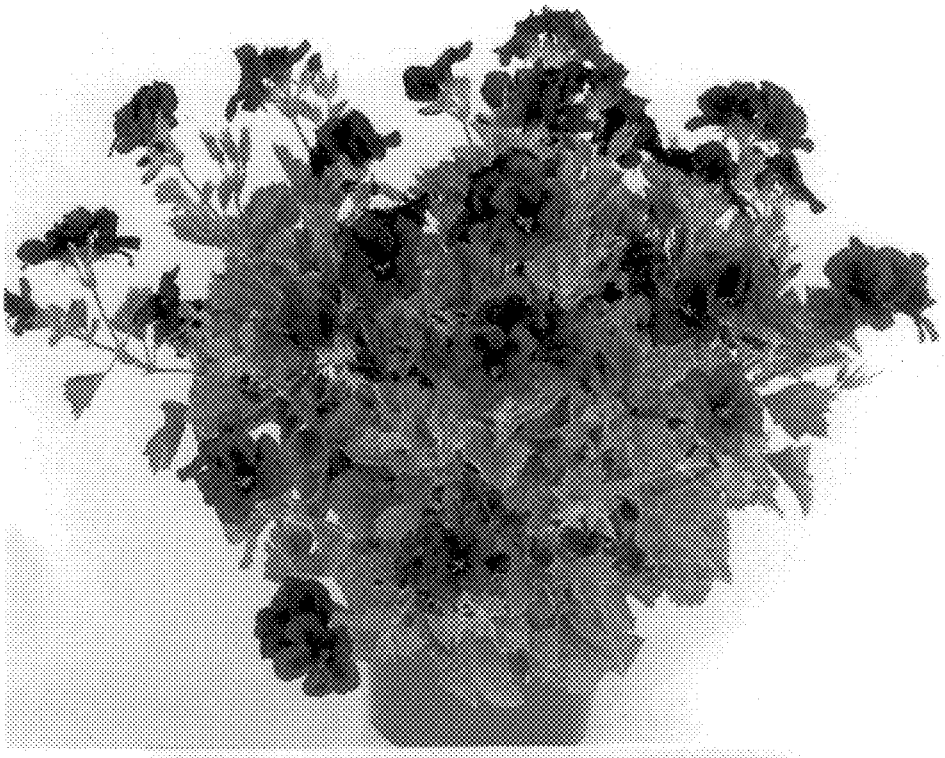
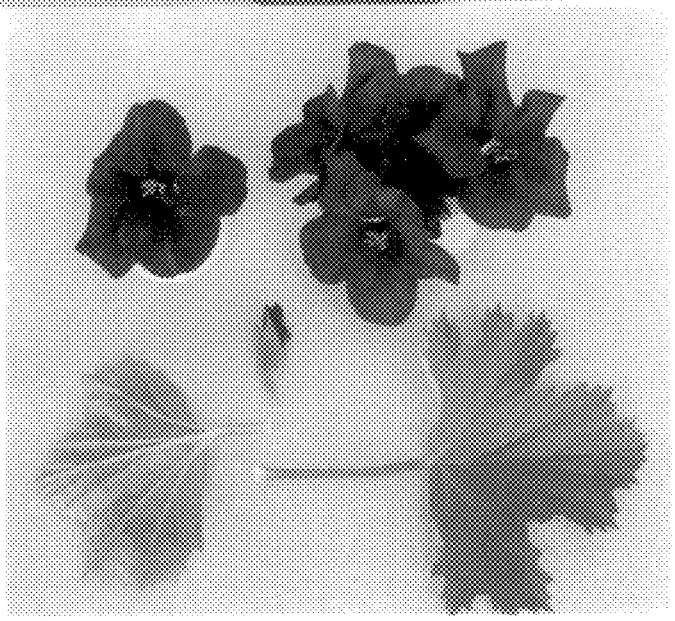

* * * * *